(12) United States Patent
Windolph

(10) Patent No.: US 6,439,068 B2
(45) Date of Patent: *Aug. 27, 2002

(54) PROCESS AND DEVICE FOR DETERMINING THE VOLUME OF LIQUID DROPLETS

(76) Inventor: Herbert Windolph, Hochstädther Weg 10, D-37115 Duderstadt (DE)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/147,731

(22) PCT Filed: Aug. 29, 1997

(86) PCT No.: PCT/EP97/04720

§ 371 (c)(1),
(2), (4) Date: Oct. 4, 1999

(87) PCT Pub. No.: WO98/09151

PCT Pub. Date: Mar. 5, 1998

(30) Foreign Application Priority Data

Aug. 31, 1996 (DE) .......................... 196 35 348

(51) Int. Cl.[7] .............................................. G01N 13/02
(52) U.S. Cl. ...................................................... 73/865.5
(58) Field of Search ............................... 73/149, 865.5; 324/71.4, 658, 686, 688

(56) References Cited

U.S. PATENT DOCUMENTS 4,569,226 A  2/1986 Matteson
4,697,451 A  10/1987 Matteson

FOREIGN PATENT DOCUMENTS

| DE | 26 53 166 | 6/1977 |
| DE | 39 22 952 | 1/1991 |
| DE | 196 35 348 | 3/1998 |
| EP | 0 286 419 | 10/1988 |

OTHER PUBLICATIONS

JP 5–149769 (A). In: Patent Abstract of Japan, Section P, vol. 17 (1993), No. 536 (P–1620), Sep. 27, 1993.
JP 3–165219 (A). In: Patent Abstract of Japan, Section P, vol. 15 (1991), No. 410 (P–1264), Oct. 18, 1991.

*Primary Examiner*—Robert Raevis
(74) *Attorney, Agent, or Firm*—Schlesinger, Arkwright & Garvey LLP

(57) ABSTRACT

First a liquid volume is comminuted into individual droplets in order to measure the volume of liquid droplets, then an electric potential different from that of the ambience is applied to the droplets, said potential determining the droplet charge as a function of its capacitance to its ambience. Finally, after charge to voltage conversion and measuring this capacitance-dependent value, the capacitance and the volume of such a drop can be determined. A liquid drop collecting vessel (2, 40) is provided for that purpose and comprises a droplet dripper (4, 42) to deliver individual droplets, further a device to charge the individual droplets formed by the drippers (4, 42). A measurement device (8, 44) is mounted underneath the liquid droplet collector vessel (2, 42) and is connected to a droplet collector electrode (16, 46) to determine the droplet capacitance by means of a voltage jump or a derivative test value. An analyzer determines the droplet volume from the measured voltage jump or from the derivative test value.

24 Claims, 2 Drawing Sheets

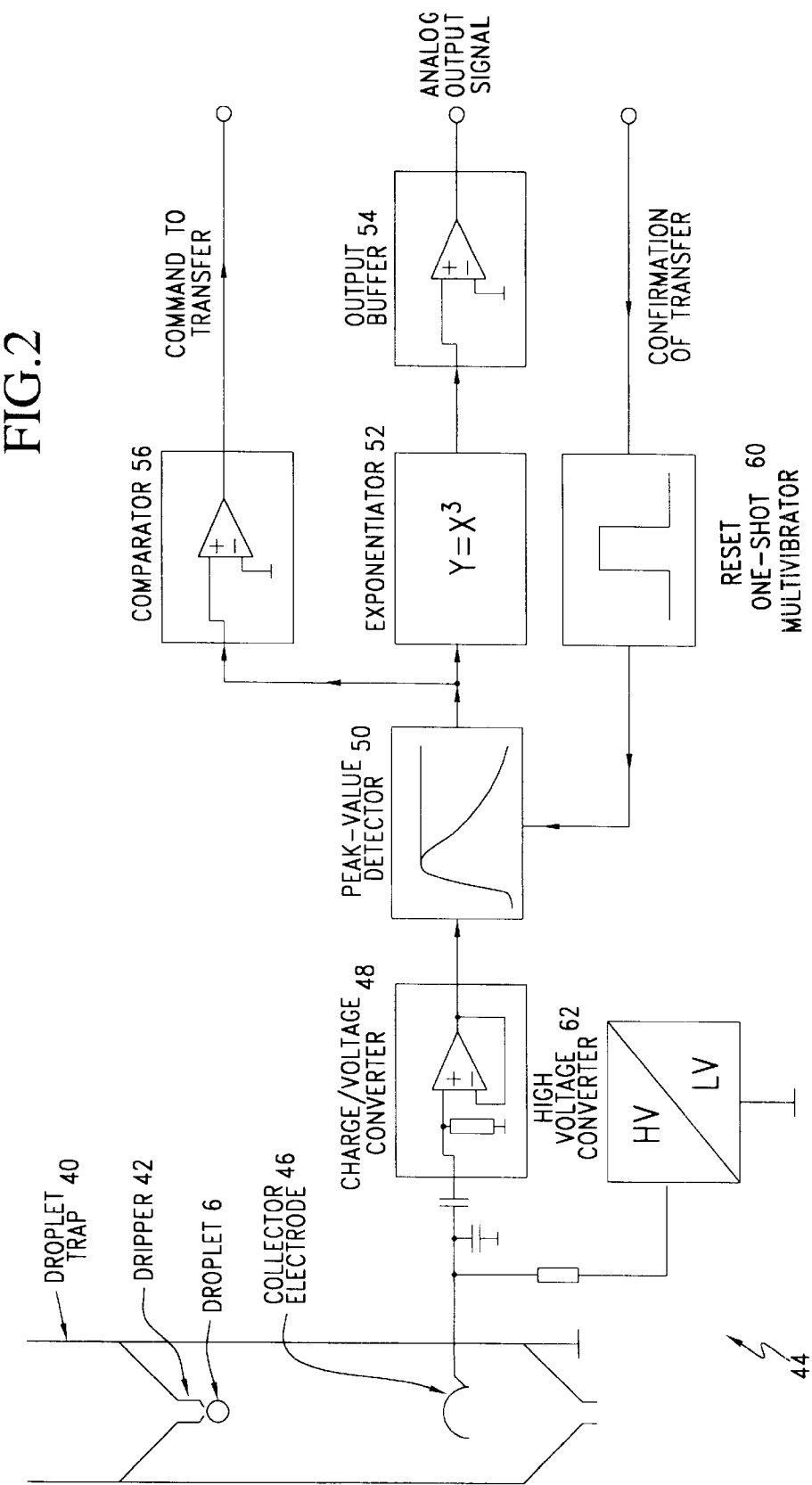

PROCESS AND DEVICE FOR DETERMINING THE VOLUME OF LIQUID DROPLETS

FIELD OF THE INVENTION

The present invention relates to a process and device, herein a method and apparatus with which to determine the volumes of liquid droplets, in particular to determine the quantities of precipitates.

BACKGROUND OF THE INVENTION

High requirements on measurement techniques are placed on reliable determination of volumes of minimal liquid quantities in droplet form. The measurement range is approximately 1 μltr to the maximum drop size. It is known to determine volume by weighing, but this procedure requires scales for comparatively small forces which are susceptible to such interference as air flows, temperature changes, microphonics etc. Using weighing, it is practically impossible to measure the particular volume of each droplet when such droplets follow each other rapidly.

It is further known to ascertain the droplet volume optically by analyzing the image of the droplet shape by resort to their shadows or using similar procedures. In such tests, optical transparency (particle-induced changes in transmission) and reflectivity of the liquid droplet negatively affect measurement accuracy.

Apparatus to measure the boundary-layer tension between two liquids of different densities is known from U.S. Pat. Nos. 4,697,451 and 4,569,226. The two liquids are present inside a cylinder where they form a boundary layer. Using a pipette, one liquid is dripped into the other underneath latter's liquid level. The pipette is made of an electrically conducting material and is connected to a voltage source. The liquid in the lower part of the cylinder is connected to an electrometer time-integrating the charge of the transiting liquid droplets. Furthermore the drop frequency is transmitted through the electrometer. Using a variable voltage source, the boundary-layer capacitance of the droplets formed in the liquid is indirectly determined iteratively from the slope of a straight line.

The European patent document A 0,286,419 describes apparatus with which to measure the pH value of a solution. Droplets are formed at the end of fiber optics, the end of the fiber optics being located between the plates of a capacitor.

The German patent document A 26 53 166 discloses apparatus with which to measure the concentration of components in a flowing liquid. This apparatus makes use of the electrokinetic effect. The liquid is converted into a stream of droplets transporting the generated stream drained by a drain electrode of a collecting vessel. Volumetry of the droplets is not provided.

OBJECTS AND SUMMARY OF THE INVENTION

The objective of the present invention is to create such a method and apparatus that liquid-droplet volumes can be determined more accurately and more economically.

This problem is solved by the falowing and apparatus.

Inventive method for measuring the volumes of liquid droplets is characterized by the following method steps:

separating a liquid volume into individual droplets, electrically charging the droplets relative to their ambience, such a charge being a function of the drop's potential difference and its capacitance relative to its ambience, measuring the droplet's capacitance or a value dependent on the capacitance, and determining the droplet volume from the measured potential jump or from a derivative value.

Inventive method for measuring liquid drops is characterized by the following method steps:

separating a liquid volume into individual droplets, raising the droplets to a potential different from that of their ambience, determining the droplet charges by converting the charges into voltage jumps or a test value dependent on the voltage jumps, determining the droplet capacitances from the measured voltage jump or from the test value dependent on the voltage jump, and computing droplet volumes from their capacitances.

Inventive apparatus with which to carry out the two (2) inventive methods set forth immediately above, and characterized by the following elements:

a liquid drop collecting vessel (2, 40) comprising a drop dripper (4, 42) to deliver individual drops, a device to electrically charge the individual drops formed by the dripper (4, 42), a measurement device (8, 44) mounted underneath the liquid-droplet collecting vessel (2, 42) connected to a droplet collector electrode (16, 46) to determine the capacitances of the droplets or derivative test values, and an analyzer to determine the drop volume from the measured capacitance or a derivative test value.

An inventive apparatus as set forth above, further characterized in that the droplet charging device comprises a voltage source (12, 62) connected to the liquid-drop collecting vessel (2) or to the dripper (4) or to the collector electrode (46) to charge them to an electric potential different from that of the ambience.

Inventive apparatus as set forth above further characterized in that the dripper (4) is fitted with a potential guide needle (10).

Inventive apparatus as set forth above further characterized in that the potential guide needle (10) is conductively connected to the liquid droplet trap (2), the drop being connected by this potential guide needle to the potential of the collecting vessel (2).

Inventive apparatus as set forth above further characterized in that the droplet collector electrode (16, 46) is connected to a measurement amplifier of which the output is a peak voltage value which is a function of the voltage jump caused by the change in potential at the collector electrode (16) by the droplet charge, or is proportional to the voltage jump, or is a function of the voltage jump caused by the change in capacitance of the collector electrode (46) due to the droplet capacitance or is proportional to this voltage jump.

Inventive apparatus as set forth above further characterized in that the measurement amplifier is a charge/voltage converter (20, 48).

Inventive apparatus as set forth above further characterized in that a peak voltage detector (24, 50) is connected to the measurement amplifier or charge/voltage converter (20, 48) for interim storage of the peak voltage value until ensuing analysis.

Inventive apparatus as set forth above further characterized in that it includes an exponentiator (26, 52) to raise the peak voltage value to the third power in order to provide a measurement value which is linear with the droplet volume.

Inventive apparatus as set forth above further characterized in that the peak voltage value detector (24, 50) is resettable following retrieval of the peak voltage value.

Inventive apparatus as set forth above further characterized in that the measurement device (8) includes a screening field electrode (14) enclosing the droplet's falling trajectory.

Inventive apparatus as claimed set forth above further characterized in that it comprises a compensation electrode (22) associated with the collector electrode (16) and together with the collector electrode (16) forming a capacitor of which the capacitance depends on the dielectric constants of the ambient medium and which thereby compensates capacitance changes in drops of equal sizes due to a changing dielectric constant.

Inventive apparatus as set forth above further characterized in that the voltage source (12, 62) comprises a high voltage converter.

Inventive apparatus as set forth above further characterized in that the collector electrode (46) is connected to a constant current source or, through a high resistance, to a voltage source (62).

Inventive apparatus as set forth above further characterized in that a comparator (30,56) is connected to the output of the peak value detector (24, 50) and will emit a transfer command signal in the presence of measurement values and in that the peak value detector is resettable by a one-shot multivibrator (32, 66) driven by a transfer confirmation signal.

The method of the invention makes use of the feasibility to impart charges (relative to their environment) to masses suspended in an insulated manner or floating or falling, on account of the capacities of such masses, such charges being retained for some time even without connection to a voltage source. A liquid, for example a water droplet, is charged by being made to contact an electrode at an electrical potential different from its environment the environment is, for instance, a metal plate at a potential $U_{ce}$ [2] which the droplet then also assumes. The droplet capacitance is determined by the diameter, ie the mass of the droplet and in turn determines the charge accepted by this droplet.

[2] ce=charging electrode

A charged and falling droplet retains this charge for some time and shares its charge with the capacitance of a detector electrode. The droplet's charge generates a voltage jump relative to the environment at the summed capacitance of droplet and detector electrode.

An uncharged and falling droplet increases the capacitance of an electrode detector at an electric potential different from its environment's according to its own capacitance, thereby generating a potential jump.

The voltage jump is measured and analyzed. Illustratively it will be amplified by a suitable measurement amplifier and will be stored in impedance-converted form in a peak-value detector, whereafter it can be analyzed at a convenient time. After considering the cubic relation between radius and volume of a sphere, a test value is obtained which is directly proportional to volume, assuming of course that the droplet is approximately spherical.

The capacitance C of a sphere of radius R in space is given by $C=4\pi\epsilon_{0(r)}R$, where $\epsilon_{0(r)}$ is the electric field permittivity constant.

Together with the (imparted) potential difference, the capacitance C determines the electric charge Q of the droplet according to the expression Droplet charge $Q=C_d U_{ce}$ where $C_d$ is the droplet capacitance.

The droplet charge relative to its environment illustratively can be measured, using a charge/voltage converter, after the droplet makes contact with a detector or collector electrode. For instance the voltage that upon droplet impact on the detector or collector electrode and that will appear at the capacitance of this electrode and at the input of an operational amplifier and will decay according to the time constant of the input impedance, can be measured as a peak value:

Measured peak voltage $U=[C_d/(C_{me}+C_d)]U_{ce}$ [3]

[3] me=measurement electrode

The volume or the mass of the droplet can be calculated from the value of the measured charge at constant known potential difference $U_{ce}$ of the charging electrode. Because of the cubic relation between radius and sphere volume, the potential values must be to the third power to lead to a test value which is linear with volume.

The invention is elucidated below in relation to the drawing showing illustrative embodiments.

BRIEF DESCRIPTION OF THE DRAWINGS

FIG. 2 is a functional diagram of a second embodiment of apparatus to measure the volume of liquid drops.

DETAILED DESCRIPTION OF THE PREFERRED EMBODIMENTS

Figure 1:
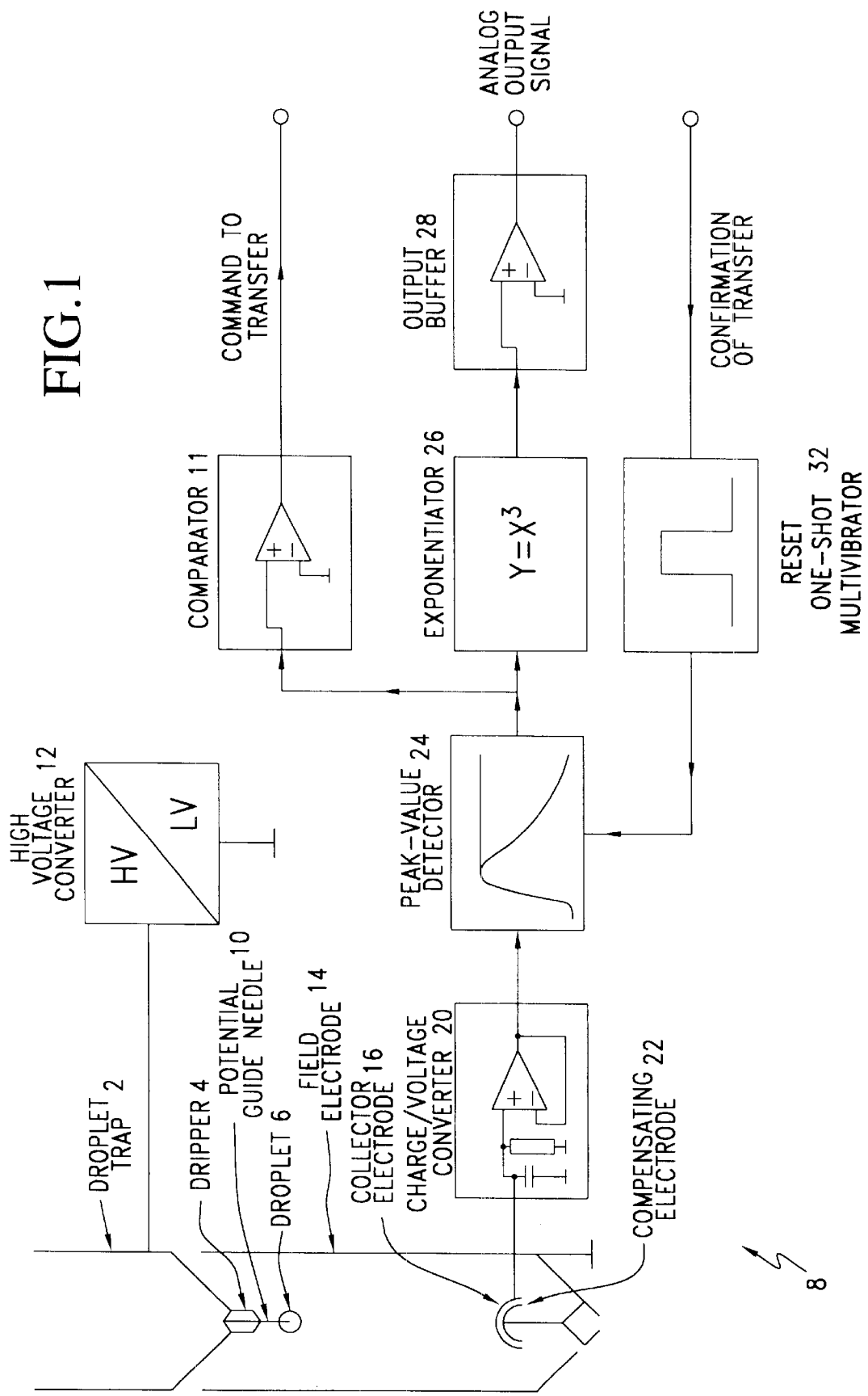
FIG. 1 is a functional diagram of a first embodiment of the invention of apparatus measuring the volume of liquid drops.

The apparatus of FIG. 1 comprises a liquid collecting vessel 2, for instance a water droplet trap collecting the amount of precipitate from a specified cross-sectional area. The collected quantity of water is supplied through a dripper 4 as a time sequence of water drops 6 fed into a test apparatus of device 8 underneath. The dripper 4 comprises a potential guide needle 10 connected through the water droplet trap 2 or directly to a voltage source, for instance a high-voltage converter 12 generating the required potential difference between the liquid collecting trap 2, ie the potential guide needle 10 and the ambience.

The test device 8 includes a droplet collector electrode 16 and an ensuing measuring electronics.

A water droplet 6 detaching from the dripper 4 assumes an approximately spherical shape. During this time the droplet is connected through the potential guide needle 10 to the potential of the droplet trap, that is, the droplet is in electrical contact with the droplet trap when already in its round shape. The required potential difference of the collector 2 relative to the ambience is generated by the high-voltage converter 12.

The potential guide needle 10 consists of an electrically conducting, hydrophobic material that shall only minimally deform the droplet when latter is detaching. The potential guide needle 10 assures accurate detachability of the droplet.

Following detachment, the droplet drops from the potential guide needle and carries with it a charge resulting from its capacitance to its environment and the potential of the water droplet trap 2 or the potential guide needle 10.

The droplet falls through the coaxial field of a field electrode 14 which will not affect the droplet capacitance to its environment even when there are slight deviations of the droplet's fall from the ideal vertical path. The field electrode offers screening against external effects. This field electrode may generate a coaxial or other field to improve apparatus behavior. The field electrode 14 may be at another electric potential than the dripper 4 or the collector electrode 16.

As the droplet nears the collector electrode 16, namely shortly before impact, it loses part of its stored electrical energy because it moves in that region together with the electric field. However this effect does not impair measurement accuracy because this change of energy behaves proportionally with each droplet size, ie each particular capacitance.

When the droplet 6 impacts the collector electrode 16, it shares its charge with a first the capacitance of this collector electrode 16 and with the input capacitance of a measurement amplifier, for instance of a charge/voltage converter 20. The first capacitance is formed between collector electrode 16 and field electrode 14, and the input capacitance is formed between charge/voltage converter 20 and ground, as will be readily appreciated. These capacitances are charged as a function of the electrical energy in the form of droplet charge and capacitance. As a result a voltage jump is created at the input of the charge/voltage converter 20.

To compensate for substantial fluctuations in the dielectric constant $\epsilon$ of the ambient air for instance on account of changes in humidity and temperature, a compensating electrode 22 may be used which together with the collector electrode 16 shall form a capacitor of-which the capacitance depends on the dielectric constant $\epsilon$ of the ambient medium and thereby compensates capacitance changes in droplets 6 of constant size due to changing dielectric constants, that is, of which the capacitance with the ambience changes proportionately to that of the droplet.

The output of the charge/voltage converter 20 goes to a peak voltage detector 24 storing the voltage peaks for further processing. To obtain an output value proportional to volume, this peak value may be raised to an exponent of 3 by an exponentiator 26. An analogue volume-proportional measurement value is then, available at the output of an output buffer 28. The output of the peak detector can command to a transfer through a comparator 11. After retrieving the analogue measurement value for instance from an external data logger, the peak value detector can be erased for instance by returning a transfer confirmation to a reset one-shot multivibrator 32.

The apparatus of FIG. 2 comprises a liquid droplet trap 40 for instance a water drop in which the quantity of precipitate from a given cross-sectional area is collected. The collected quantity of water is fed by means of a dripper 42 as a time sequence of water droplets into a measurement device 44 underneath. The measurement device 44 comprises a collector electrode 46 connected to a measurement amplifier, for instance a charge/voltage converter 48.

When a droplet detaches from the dripper 42, this droplet already assumes a nearly spherical shape. While the droplet falls through its path to the collector electrode 46, its sphericity improves further. The speed acquired by the droplet over the comparatively short fall trajectory does not yet entail significant warping of its spherical shape.

When the droplet falls after detaching off the dripper 42, it bears no charge relative to the ambient because the droplet trap is at the same potential as the ambience.

The collector electrode 46 is at a potential different from the ambience due to a voltage source, for instance a high-voltage converter 62 being connected through a large resistance to it or by an omitted constant-current source being applied to it.

When the droplet impacts the collector electrode 46, the capacitance of this electrode 46 to the ambience is enlarged (i.e., the capacitance formed by the collector electrode 46 acting as an electrode and the droplet trap 40 acting as a further electrode, as will be readily appreciated, also to the coupling capacitance with respect to the charge/voltage converter 48. As a result a voltage jump is generated at the collector electrode 46 and at the input of the charge/voltage converter 48. The output of the charge/voltage converter 48 is fed into a peak voltage detector 50 storing the voltage peak for subsequent processing.

To obtain an output value proportional to volume, said peak value can be raised to the third power using an exponentiator 52.

The analogue volume-proportional measured value is available at an output buffer. The output from the peak detector 50 can emit a transfer command through a comparator 56.

After retrieving the analogue measured value for instance from an external data logger, the peak detector can be erased by returning a transfer confirmation to a reset, one-shot multivibrator 60.

The peak detector 24 or 48 may be eliminated if an adequately large decay time-constant is achieved by means of a very high input resistance at the charge/voltage converter 20 or 48 or if digital peak measurements are carried out using an A/D converter.

Illustratively the collector electrode 16 or 46 is planar, convex or concave. It may also be made of a foil or be in the form of a grid.

what is claimed:

1. Apparatus for measuring the volumes of liquid droplets, comprising:
    a) a liquid droplet collecting vessel including a droplet dripper to deliver falling individual droplets;
    b) a droplet charging device to electrically charge the individual droplets formed by the dripper;
    c) a measurement device mounted underneath the liquid droplet collecting vessel and connected to a droplet collector electrode to determine capacitances of falling droplets which fall from the droplet dripper or values dependent on the capacitances of the droplet;
    d) a screening field electrode which encloses the falling droplets; and
    e) an analyzer to determine the droplet volume from the capacitances or the values dependent on the capacitances determined by the measurement device.

2. Apparatus as claimed in claim 1, wherein:
    a) the droplet charging device includes a voltage source connected to the liquid droplet collecting vessel or to the droplet dripper or to the collector electrode to charge them to an electric potential different from that of the ambience.

3. Apparatus as claimed in claim 1, wherein:
    a) a constant voltage source is provided, the constant voltage source provides a constant voltage to the droplet collector electrode.

4. Apparatus as in claim 1, wherein:
    a) the analyzer includes a peak voltage detector.

5. A method for measuring liquid droplets, comprising the following steps:
    a) providing a volume of liquid;
    b) separating the liquid volume into individual droplets;
    c) raising the droplets to a potential different from that of their ambience;
    d) determining the droplet charges by converting the charges into measured voltage jumps or a test value dependent on the measured voltage jumps;

e) determining the droplet capacitances from the measured voltage jumps or from the test value dependent on the measured voltage jumps;

f) the step of determining the droplet capacitances is carried out at a constant voltage; and g) computing droplet volumes from their capacitances.

6. Method as in claim 5, comprising the step of:

a) providing a coaxial field to screen the droplets against external effects.

7. Apparatus with which to carry out the method claimed in claim 5, wherein:

a) a liquid droplet collecting vessel is provided which comprises a droplet dripper to separate and deliver individual droplets;

b) a droplet charging device is provided which electrically charges the individual droplets formed by the dripper;

c) a measurement device is mounted underneath the liquid droplet collecting vessel and connected to a droplet collector electrode to determine a measured capacitances of the droplets or measured test values dependent on the capacitances; and d) an analyzer is provided to determine the droplet volume from the measured capacitances or the measured test values dependent on the capacitances.

8. Apparatus as claimed in claim 7, wherein:

a) the droplet charging device includes a voltage source connected to the liquid droplet collecting vessel or to the dripper or to the collector electrode to charge liquid droplets to an electric potential different from that of the ambience.

9. Apparatus as claimed in claim 8, wherein:

a) the voltage source includes a high voltage converter.

10. Apparatus as claimed in claim 7, wherein:

a) the collector electrode is connected to a constant current source or, through a high resistance, to a constant voltage source.

11. Apparatus as claimed in claim 7, wherein:

a) a measurement amplifier is connected to the droplet collector electrode, the measurement amplifier provides an output which is a peak voltage value that is a function of the voltage jump caused by the change in potential at the droplet collector electrode by the droplet charge, or is proportional to the voltage jump, or is a function of the voltage jump caused by the change in capacitance of the droplet collector electrode due to the droplet capacitance.

12. Apparatus as claimed in claim 11, wherein:

a) the measurement amplifier is a charge/voltage converter.

13. Apparatus as claimed in claim 11, wherein:

a) a peak voltage detector is connected to the measurement amplifier for interim storage of the peak voltage value until ensuing analysis.

14. Apparatus as claimed in claim 13, wherein:

a) the peak voltage detector is resettable following retrieval of the peak voltage value.

15. Apparatus as claimed in claim 13, wherein:

a) a comparator is connected to the output of the peak voltage detector, and the comparator emits a transfer command signal in the presence of measurement values, and the peak voltage detector is resettable by a one-shot multivibrator driven by a transfer confirmation signal.

16. Apparatus as claimed in claim 11, wherein:

a) an exponentiator is provided to raise the peak voltage value provided by the measurement amplifier to the third power, in order to provide a measurement value which is linear relative to the droplet volume.

17. Apparatus as claimed in claim 11, wherein:

a) a compensation electrode is associated with the droplet collector electrode and together with the collector electrode forms a capacitor of which the capacitance depends on the dielectric constants of the ambient medium and which thereby compensates capacitance changes in drops of equal sizes due to a changing dielectric constant.

18. Apparatus as claimed in claim 7, wherein:

a) a screening field electrode is provided, the screening field electrode provides the coaxial field and encloses a falling droplet's trajectory.

19. Apparatus as claimed in claim 5, wherein:

a) a potential guide needle is provided.

20. Apparatus as claimed in claim 19, wherein:

a) the potential guide needle is conductively connected to the liquid droplet collecting vessel, so that in use a droplet is connected by the potential guide needle to the potential of the collecting vessel.

21. An apparatus, comprising:

a) a liquid droplet collecting vessel being provided which comprises a droplet dripper to separate and deliver individual droplets from a volume of liquid;

b) a droplet charging device being provided which electrically charges the individual droplets formed by the dripper relative to their ambience to provide an electrical charge, the electrical charge being a function of the droplet's potential difference and their capacitance relative to their ambience;

c) a measurement device being mounted underneath the liquid droplet collecting vessel and connected to a droplet collector electrode to determine a measured capacitances of the droplets or measured test values dependent on the capacitances;

d) a coaxial field being provided to screen the droplets against external effects;

e) an analyzer being provided to determine the droplet volume from the measured capacitances or the measured test values dependent on the capacitances;

f) a potential guide needle being provided; and g) the potential guide needle being conductively connected to the liquid droplet collecting vessel, so that in use a droplet is connected by the potential guide needle to the potential of the collecting vessel.

22. An apparatus comprising:

a) a liquid droplet collecting vessel being provided which comprises a droplet dripper to separate and deliver individual droplets;

b) a droplet charging device being provided which electrically charges the individual droplets formed by the dripper relative to their ambience to provide an electrical charge, the electrical charge being a function of the droplet's potential difference and their capacitance relative to their ambience;

c) a measurement device being mounted underneath the liquid droplet collecting vessel and connected to a droplet collector electrode to determine a measured capacitances of the droplets or measured test values dependent on the capacitances;

d) a coaxial field being provided to screen the droplets against external effects, the coaxial field including a screening field electrode enclosing a falling drop's trajectory; and e) an analyzer being provided to determine the droplet volume from the measured capacitances or the measured test values dependent on the capacitances.

23. An apparatus, comprising:

a) a liquid droplet collecting vessel being provided which comprises a droplet dripper to separate and deliver individual droplets;

b) a droplet charging device being provided which electrically charges the individual droplets formed by the dripper relative to their ambience to provide an electrical charge, the electrical charge being a function of the droplet's potential difference and their capacitance relative to their ambience;

c) a measurement device being mounted underneath the liquid droplet collecting vessel and connected to a droplet collector electrode to determine a measured capacitances of the droplets or measured test values dependent on the capacitances;

d) a coaxial field being provided to screen the droplets against external effects;

e) an analyzer being provided to determine the droplet volume from the measured capacitances or the measured test values dependent on the capacitances;

f) a measurement amplifier being connected to the droplet collector electrode, the measurement amplifier providing an output which is a peak voltage value that is a function of the voltage jump caused by the change in potential at the droplet collector electrode by the droplet charge, or is proportional to the voltage jump, or is a function of the voltage jump caused by the change in capacitance of the droplet collector electrode due to the droplet capacitance; and g) a compensation electrode being associated with the droplet collector electrode and together with the collector electrode forming a capacitor of which the capacitance depends on the dielectric constants of the ambient medium and which thereby compensates capacitance changes in drops of equal sizes due to a changing dielectric constant.

24. An apparatus, comprising:

a) a liquid droplet collecting vessel being provided which comprises a droplet dripper to separate and deliver individual droplets from a volume of liquid;

b) a droplet charging device being provided which electrically charges the individual droplets formed by the dripper relative to their ambience to provide an electrical charge, the electrical charge being a function of the droplet's potential difference and their capacitance relative to their ambience;

c) a measurement device being mounted underneath the liquid droplet collecting vessel and connected to a droplet collector electrode to determine a measured capacitances of the droplets or measured test values dependent on the capacitances;

d) a coaxial field being provided to screen the droplets against external effects;

e) an analyzer being provided to determine the droplet volume from the measured capacitances or the measured test values dependent on the capacitances;

f) a measurement amplifier being connected to the droplet collector electrode, the measurement amplifier providing an output which is a peak voltage value that is a function of the voltage jump caused by the change in potential at the droplet collector electrode by the droplet charge, or is proportional to the voltage jump, or is a function of the voltage jump caused by the change in capacitance of the droplet collector electrode due to the droplet capacitance;

g) a peak voltage detector being connected to the measurement amplifier for interim storage of the peak voltage value until ensuing analysis; and h) a comparator being connected to the output of the peak voltage detector, and the comparator emiting a transfer command signal in the presence of measurement values, and the peak voltage detector being resettable by a one-shot multivibrator driven by a transfer confirmation signal.

* * * * *